United States Patent [19]

Yamada et al.

[11] Patent Number: 5,126,135
[45] Date of Patent: Jun. 30, 1992

[54] DERMATOLOGICAL COMPOSITION BASED ON AN AQUEOUS PHASE

[75] Inventors: Hajime Yamada; Akira Yamada, both of Nagareyama, Japan

[73] Assignee: Japan Fine Chemical Co., Ltd., Nagareyama, Japan

[21] Appl. No.: 717,073

[22] Filed: Jun. 18, 1991

[51] Int. Cl.⁵ .................. A61K 7/48; A61K 9/06; A61K 31/70; A61K 33/14
[52] U.S. Cl. .................. 424/401; 424/678; 424/679; 424/680; 426/658; 514/858; 514/859; 514/864; 514/886; 514/887
[58] Field of Search ......................... 424/401

[56] References Cited

U.S. PATENT DOCUMENTS 4,921,701  5/1990  Blank .......................... 424/401
5,000,939  3/1991  Dring .......................... 424/48

OTHER PUBLICATIONS

Budavari et al. (1989), The Merck Index, Merck & Co., Inc.

Primary Examiner—Thurman K. Page
Assistant Examiner—Raj Bawa
Attorney, Agent, or Firm—Kane, Dalsimer, Sullivan, Kurucz, Levy, Eisele and Richard

[57] ABSTRACT

The present invention relates to a dermatological composition composed for cosmetics or medicines for external application to skin and to oral or nasal mucous-membrane. This composition can be applied in particular in the cosmetic or pharmaceutical field, especially in the dermatological cases to regenerate and to revitalize damaged cells by equilibrating electrochemical ion gradients across cell membrane and also by osmotic pressure on the inner face of the cell membrane. A composition based on a water phase in accordance with present invention comprises dextran, glucose, mutan lentinan, NaCl, KCl, and $CaCl_2$, which are dissolved in the aqueous phase.

4 Claims, No Drawings

DERMATOLOGICAL COMPOSITION BASED ON AN AQUEOUS PHASE

BACKGROUND OF THE INVENTION

The present invention relates to a dermatological composition composed for external application to skin and to oral or nasal mucous-membrane. This composition can be applied in particular in the cosmetic or pharmaceutical field, especially in the dermatological cases to regenerate and to revitalize damaged cells by equilibrating electrochemical ion gradients across cell membrane and also by osmotic pressure on the inner face of the cell membrane. The osmotic pressure thereon is counterbalanced by osmotic pressure exerted by the molecules chiefly Na and Cl in the extracellular fluid.

In recent years, there has been remarkable advances in developing cosmetic or pharmaceutical compositions, especially dermatological compositions used for external application to skin or mucous membrane, and various kinds of such compositions were developed which contribute to be treatment of some of the skin disorders. Most of these conventional compositions are dispensed in the form of liquid, for example face lotion, or in the form of cream, ointment or the like, by mixing an essential composition with a base material such as methyl cellulose, synthetic-resin emulsion, polyethylene glycol, powder or the like.

Furthermore there has been a demand for a dermatological composition as a barrier for protecting the surface of skin from drying, wetting, exposuring to glaring sunlight or ultraviolet light, or other environmental factors.

All living cells and their cell-organelle are protected from their surroundings by biological membranes having selective permeabilities against simple ions, sugars and the like. The selective permeabilities of biological membranes, for example the permeability to simple ions such as Na and K, creates large differences in the ionic composition of the cell-interior compared to the extracellular fluid, and thus this enables cell membranes to store potential energy in the form of ion gradients which can be observed by the membrane potential. Therefore the transmembrane ion gradients make ATPs (adenosine 5'-triphosphates) which are responsible to drive various transport processes and to transmit electrical signals across the membrane.

Furthermore, the membrane potential that exists across the cell membrane is maintained by a Na-K pump which generates K and Na concentration gradients in opposite directions of the membrane. The Na-K pump links with the Na-K ATPase which helps not only maintaining of the electrical potential across the membrane but also regulating of the cell volume. The Na-K ATPase controls the solute concentrations inside the cell and thereby the osmotic forces that would tend to make the cell swell or shrink.

But for the most cells of multicellular animals, the Na-K ATPase is crucial, so that the cell for example a human blood-cell or a bacterial cell can be shrinked when it exposed to hypertonic solution. In contrast, the cell can be swollen or lysed when it exposed to hypotonic solution. Thus the solute concentration of the extracellular space should be regulated.

Accordingly, when the surface of skin is damaged by the above mentioned factors, the equilibrium of the ionic gradients across cell membrane of the skin can be destroyed. For restoring the ionic equilibrium state across the membrane, an appropriate ionic composition should be applied to the extracellular space.

It is known that NaCl shows an important role for maintaining the above described equilibrium between the inside (cytoplasm) and the outside (extracellular space) of the cell.

In the case of a human body fluid, for example, 0.9% NaCl solution is isotonic with the extracellular fluid and thus it is used as an isotonic sodium chloride solution or a physiological saline in the medical field.

In an animal body, glucose is usually converted into glycogen and stored in liver or muscle as an energy source or nutrition source for the vital cells, and also glucose is usually lysed in the process known as glycolysis. In this process, a glucose molecule with six carbon atoms is converted into two small molecules of pyruvate which enters the mitochondria to be completely oxidized to $CO_2$ and $H_2O$ and to generate ATP required for many biosyntheses. Accordingly, it has been known that glucose is the principal food compound of many cells. In the course of glucose breakdown as described above, energy is produced and used to drive biosynthetic reactions and to other energy-requiring processes in the cell. Therefore, it is preferable to administrate glucose in the form of a liquid to an animal by oral, intravenous, or intramuscular administration.

In the case of blood plasma which is easily isolated from an animal body, it has been known that the blood plasma permeates though skin and mucous membrane and thus it plays an essential role in the skin-restoration processes when it is applied on the surface of skin. Accordingly, the isolated-plasma is used as an ingredient of a medicine for external application.

To protect the skin from the above described injurious factor, some of the conventional cosmetics or medicines comprise an inorganic salt such as sodium chloride, glucose or one of the other natural sugars, or a blood plasma fraction.

In the document of U.S. Pat. No. 3574854, for example, a dermatological composition in the form of cream has been disclosed. This composition comprises NaCl as an ingredient for restoring the damaged skin to be soft to the touch. Also the document of German Paten Application No. 3327840 discloses a dermatological composition comprising a mineral salt as an ingredient for sterilizing or disinfecting the surface of ski from the bacterial contamination. Furthermore U.S. Pat. No. 3859436 discloses a dermatological composition comprising glucose as an ingredient for smoothing the surface of skin, and in addition U.S. Pat. No. 3777597 discloses a dextran solution for a shaving lotion or the like.

Accordingly, these conventional dermatological compositions has been used as cosmetics or medicines for external application to protect the surface of skin from the above described injurious factors.

As described above, the conventional dermatological compositions have been recognized as biological components for maintaining physiological functions of cell. However, the conventional dermatological composition shows several disadvantages:

(1) in the case of a dermatological composition comprising NaCl for killing bacteria or the like, water can be lost from the skin cell having excess of sodium;

(2) in the case of a dermatological composition comprising glucose or the other natural sugar, topically-applied glucose cannot be breakdown into simple substances because glucose is not absorbed from the surface of skin: and (3) in the case of a dermatological composition comprising blood plasma isolated from human or animal body, the isolated-plasma is easily denatured and thus it must be mixed with polyethylene glycol as a protecting agent when it is used as an ingredient of the medicine (remarkably, polyethylene glycol must be included in at least more than 60% of a total weight of the medicine to protect proteins such as serum protein, coagulation proteins and the like contained in the plasma).

Accordingly, the conventional compositions as described above are difficult to comprise in a medicine for external application for restoring physiological disorders of skin cells. In addition, the conventional compositions as described above are unsuitable for treating some of dermatological disease such as athlete's foot, offensive smell of the armpit, baldness, scurf, itching, or the like, which are caused by inhibiting blood circulation in capillary vessel in the skin and by arresting cell division of the skin cells.

To solve the above problems, we found the dermatological composition a disclosed in Japanese Patent Application TOKKAISHO 61-24630). It discloses a dermatological composition which is responsible for recovering physiological functions of damaged skin by equilibrating electorochemical ion gradients and osmotic forces across cell membrane. In addition, this composition facilitates the cell division and shows preferable effects on restoring pigmentation and erubescent face. Thus the dermatological composition according to the above reference can be comprised in lotion and shows regenerating or revitalizing activity to the skin when it is applied on face, hand, hair or the other regions except mucous membrane.

SUMMARY OF THE INVENTION

It is therefore an principal object of the present invention to provide a composition used for cosmetics or medicine for external application to mucous membrane for restoring or improving dermatological symptoms such as stomatitis, pollinosis or the like.

So as to achieve the above described object, the present invention provides a composition comprising dextran, glucose, phase. Concentration of these ingredients of the composition is as follows: each concentration of dextran, glucose, mutan, and lentinan is between 5 to 30% of the weight of said composition, respectively, and each concentration of NaCl, KCl, and CaCl$_2$ is between 0.1 to 1% of the weight of said composition, respectively.

In the present invention, the percentages are given by weight, unless indicated otherwise.

Other objects, characteristics and advantages of the invention will become more clearly apparent from the following explanatory description referring to the following example, which cannot in any way limit the scope of the invention.

DESCRIPTION OF THE PREFERRED EMBODIMENTS

A composition in accordance with a preferred embodiment of the present invention comprises dextran, glucose, mutan, lenthynan, NaCl, KCl, and CaCl$_2$, dissolved in an aqueous phase. Concentration of these ingredients of the composition is as follows: each concentration of dextran, glucose, mutan, and lentinan is between 5 to 30% of the weight of said composition, respectively, and each concentration of NaCl, KCl, and CaCl$_2$ is between 0.1 to 1% of the weight of said composition, respectively.

It is preferable in these compositions according to the present invention, the above described ingredients are dissolved in an aqueous phase at a temperature of between 50 to 100° C. and the aqueous phase should be a pure water which does not contain any oily material such as a detergent or the like.

In accordance with the preferred embodiments of the present invention, a cosmetic or pharmaceutical substance, especially dermatological substance comprises a composition based on an aqueous phase, wherein dextran, glucose, mutan, and lentinan is dissolved in the aqueous phase.

It is preferable that the above described composition based on an aqueous phase further comprises NaCl, KCl, and CaCl$_2$. In this composition, these ingredients are dissolved in the aqueous phase.

In accordance with another preferred embodiment of the present invention, a cosmetic or pharmaceutical substance, especially dermatological substance, wherein dextran, glucose, mutan, lenthynan, NaCl, KCl, and CaCl$_2$ dissolved in the aqueous phase and each concentration of these ingredients is as follows, each concentration of dextran, glucose, mutan, and lentinan is between 5 to 30% of the weight of the composition, respectively, and each concentration of NaCl, KCl, and CaCl$_2$ is between 0.1 to 1% of the weight of the composition, respectively.

It is preferable in these cosmetic or pharmaceutical substances according to the present invention, the above described ingredients are dissolved in the aqueous phase at a temperature of between 50 to 100° C. and the aqueous phase should be a pure water which does not contain any oily material such as a detergent or the like.

EXAMPLE

Table 1 shows a composition in accordance with a preferred embodiment of the present invention. These ingredients shown in the table 1 were dissolved in a distilled water at 50°-100° C.

An obtained composition is used as a medicine for external application The efficiencies of the composition against various kinds of skin disorders were assayed as follows.

540 patients suffered from one of the skin disorders were grouped into each corresponding symptom as described in table 2.

A suitable amount of the above described composition was administrated to each patient for 6 months and after that the efficiencies of the composition were estimated as follows. A patient who did not show an improvement of the symptom made no point of efficiency; a patient who showed any improvement of the symptom made one point of efficiency; and a patient who was cured of disease made 2 points of efficiency. These individual points were summed up in each symptom and then the sum of the points were listed in table 2.

In addition, an efficiency was indicated by a rate value calculated by following formula in each symptom.

Efficiency (%) = a total of points/a total of patient × 2 × 100

TABLE 1

An amount of each ingredient of a composition according to the present invention

| ingredients | % by weight of a composition |
| --- | --- |
| dextran | 20 |
| glucose | 10 |
| mutan | 10 |
| lentinan | 10 |
| NaCl | 0.9 |
| CaCl₂ | 0.3 |
| KCl | 0.3 |
| Distilled water | 48.5 |
| total | 100.0 |

TABLE 2

The efficiencies of the composition against different symptoms

| symptoms | No. of patients | points | efficiency (%) |
| --- | --- | --- | --- |
| male pattern baldness | 60 | 118 | 98 |
| nervous baldness | 50 | 50 | 50 |
| pimples | 30 | 56 | 93 |
| erubescence face | 60 | 64 | 53 |
| athlete's foot | 50 | 94 | 93 |
| seborrheic dermatosis | 100 | 196 | 98 |
| atopic dermatosis | 100 | 94 | 47 |
| stomatis | 50 | 100 | 100 |
| allergic rhinits | 40 | 80 | 100 |

It has been shown that some of skin diseases listed in Table 2 are difficult to treat or to improve their conditions by topical application of the conventional composition.

As shown in Table 2, however, the novel composition according to the present invention is able to improve these conditions, and especially in the cases of stomatic and allergic rhinitis, 100% efficiency is obtained.

From the results of the above described assay, the present invention provides a composition which is able to equilibrate electrochemical ion gradients and osmotic forces across mucous membrane. Accordingly, the oral and nasal mucous membranes are not stimulated by the present composition and thus stomatic and allergic rhinitis is cured at 100% efficiency.

While the described embodiment represents the preferred form of the present invention. It is to be understood that modifications will occur to those skilled in that art without departing from the spirit of the invention. The scope of the invention is therefore to be determined solely by the appended claims.

What is claimed is:

1. A composition based on an aqueous phase comprising dextran, glucose, mutan, lentinan, NaCl, KCl, and CaCl₂ which are dissolved in said aqueous phase wherein the concentration of dextran, glucose, mutan and lentinan each between 50 to 30% of the weight of said aqueous phase and the concentration of NaCl, KCl, and CaCl₂ are each between 0.1 to 1% of the weight of said aqueous phase.

2. A composition according to claim 1, wherein dextran, glucose, mutan, lentinan, NaCl, KCl, and CaCl₂ are dissolved in said water phase at a temperature of between 50 to 100° C.

3. A composition according to any one of claims 1 or 2, wherein said water phase is water which does not contain any oily material.

4. A cosmetic or pharmaceutical substance, especially dermatological substance, which comprises a composition according to any one of claims 1, 2 or 3.

* * * * *